(12) United States Patent
Selling

(10) Patent No.: US 9,102,831 B1
(45) Date of Patent: Aug. 11, 2015

(54) PROCESS FOR PRODUCING IMPROVED ZEIN ARTICLES

(75) Inventor: Gordon W. Selling, Dunlap, IL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 368 days.

(21) Appl. No.: 13/609,336

(22) Filed: Sep. 11, 2012

(51) Int. Cl.
*C08H 1/02* (2006.01)
*C08L 89/00* (2006.01)
*C07K 14/425* (2006.01)
*C07K 1/107* (2006.01)
*C08F 22/04* (2006.01)
*C08F 8/46* (2006.01)
*C08F 222/08* (2006.01)

(52) U.S. Cl.
CPC ............. *C08L 89/00* (2013.01); *C07K 1/107* (2013.01); *C07K 14/425* (2013.01); *C08F 8/46* (2013.01); *C08F 22/04* (2013.01); *C08F 222/08* (2013.01); *C08H 1/02* (2013.01)

(58) Field of Classification Search
CPC ............ C08L 89/00; C08H 1/02; C07K 1/00; C07K 1/107; C07K 14/425; C08F 22/04; C08F 222/08; C08F 8/46
USPC .......................... 524/498; 424/491; 428/402.2
See application file for complete search history.

(56) References Cited

U.S. PATENT DOCUMENTS 3,116,206 A * 12/1963 Brynko et al. ................. 424/491
3,576,758 A * 4/1971 Emrick ....................... 428/402.2
7,771,528 B2 8/2010 Selling et al.

* cited by examiner

*Primary Examiner* — Ling Choi
*Assistant Examiner* — Ronald Grinsted
(74) *Attorney, Agent, or Firm* — John D. Fado; G. Byron Stover

(57) ABSTRACT

Cross-linked zein articles are prepared by a melt process where zein is mixed with polyethylene maleic anhdyride. The melt processing can be conducted as a batch process (e.g., as in a torque rheometer) or as a continuous process (e.g., as in reactive extrusion using a screw extruder). This process provides a zein article that has reduced solubility in acetic acid (a solvent that normally dissolves unaltered zein) and/or increased tensile strength.

24 Claims, 3 Drawing Sheets

PROCESS FOR PRODUCING IMPROVED ZEIN ARTICLES

BACKGROUND OF THE INVENTION

1. Field of the Invention

This invention relates to novel cross-linked zein compounds and processes for making articles from the zein. This invention specifically relates to articles made from zein that are resistant to solvents that normally dissolve zein and/or exhibit increased tensile strength, and a single step process using melt processing for their production.

2. Background of the Invention

Zein is a naturally occurring protein derived from corn, and is customarily present in the co-products of the bio-ethanol industry. It can be isolated using various techniques and purchased in substantially pure (greater than 85%) form. Compared to most proteins, zein is characterized by a relative deficiency of hydrophilic groups. In zein, the high proportion of non-polar side chains accounts for the solubility of zein in organic solvents (such as 80% Ethanol/water) and its classification as a prolamine. Zein has been shown to be readily soluble in solvents such as dimethyl formamide (A. Biswas et. al., ACS Symposium Series, 900, Polymer Biocatalysis and Biomaterials, 141-148) and acetic acid [D. Sessa et. al., J. Applied Polymer Science, 105 (5) 2877-2883; G. Selling et. al., Cereal Chemistry, 84 (3) 265-270 and G. Selling et. al., Macromolecular Chemistry and Physics, 208 (9) 1002-1010]. In order to reduce the impact solvent has on zein articles, zein has been treated with cross-linking reagents in solution, such as formaldehyde, where the reaction takes place either before or during the coagulation of the article by using an acid/inorganic salt bath. Additional formaldehyde treatments may be employed. C. B. Croston et al., describe such a process in Industrial and Engineering Chemistry, 37 (12) (1945) 1194-1198. Croston et al. call for zein solutions for spinning containing approximately 13 to 16.5% solids, in the pH range of 11.3 to 12.7. E. T. Cline describes another method for producing zein fibers from basic zein solutions in U.S. Pat. No. 2,475,879. Multiple formaldehyde treatments of zein obtained from a basic zein solution are described in producing a zein fiber by C. D. Evans and C. B. Croston in Textile Research Journal, 19, (1949) 202-211. However, in each of these cases, the zein has been dissolved in solution before treatment with a cross-linking reagent such as formaldehyde.

Recently W. Uy, U.S. Pat. No. 5,750,064, has described a non-basic zein solution which can be dry spun and after post-treatment with formaldehyde gives a resilient article. The articles from these processes have reduced solubility in most of the standard zein solvents. The solids disclosed were 40-60% and required multiple steps.

W. Uy has described the use of zein and water at high temperatures in an extruder to produce fibers. After extrusion the fibers are stabilized by passing them through a formaldehyde containing bath to give articles with reduced solubility (U.S. Pat. No. 5,580,499). However, the % solids described in this technique is very low which would limit the productivity of the process. In addition the process described is a multi-step process.

T. McMeekin et. al. describes the production of zein fibers by extruding a mixture of approximately 55-62% zein, with the remainder being water, through an extruder having a die with holes of the desired diameter. The resulting fibers were then post-treated with formaldehyde by passing them through a bath(s) having suitable reagents. In this process, the maximum zein concentration is 62% and the process requires multiple chemical treatments where the first step is mixing with water followed by multiple 'hardening' steps through treatment with formaldehyde.

Y. Yang et. al. describes the use of citric acid for cross-linking zein in solution in the Journal of Biomaterials Science 22 (2011) 1393-1408 and Acta Biomaterialia 6 (2010) 4042-4051. The resulting materials have resistance to water, but there is no mention of resistance to known zein solvents. In addition this process is performed in water which would necessitate the handling of solution waste.

G. Selling et. al. describes the use of glyoxal in solution to cross-link zein in the Journal of Applied Polymer Science, 123 (2012) 2651-2661 and Journal of Biobased materials and Bioenergy, 1 (2007) 281-287. This work requires the use of solvent, necessitating handing solvent waste. The same author describes the use of glyoxal in a melt, without solvent, in a batch process [Journal of Applied Polymer Science, 109 (2008) 2375-2383] and using reactive extrusion [Journal of Applied Polymer Science, 113 (2009) 1828-1835 and U.S. Pat. No. 7,771,528]. These techniques provide zein articles with improved resistance to known good solvents of zein, and can be performed in a melt process which avoids solvents and the handling of large amounts of liquid waste. However, glyoxal is a toxic volatile material.

D. Sessa et. al. describes the use of glutaraldehyde in solution [Journal of Applied Polymer Science 105 (2007) 2877-2883 and Macromolecular Chemistry and Physics 209 (2008) 1003-1011]. This work requires the use of solvent necessitating handing solvent waste. The same author describes the use of glutaraldehyde in the melt, without solvent, in a batch process [Journal of Agricultural and Food Chemistry, 56 (2008) 7067-7075]. As with the processes of G. Selling above, these techniques provide zein articles with improved resistance to known good solvents of zein and can be performed in a melt process thereby avoiding solvents and the handling of large amounts of liquid waste. However, glutaraldehyde is also a toxic volatile material.

Despite these and other advances, the need remains for an improved process for making articles from zein with limited solubility, using less toxic and less volatile reagents.

SUMMARY OF THE INVENTION

I have now discovered novel polymeric compounds which comprised of zein protein cross-linked with polyethylene maleic anhydride (PEMA). These zein polymers and articles prepared therefrom have limited solubility in standard solvents such as acetic acid, or increased tensile strength, or both. The PEMA cross-linked zein polymers may be produced in a single step using a melt process. In this process, zein, which is typically in a solid phase, is mixed with PEMA in an amount effective to cross-link the zein and heated at a temperature with shear and for a period of time effective to form a melt of zein and PEMA, effectively forming cross-links. A plasticizer is preferably also added to the zein/PEMA reaction mixture to increase the flowability and thermoplasticity of the materials for ease of mixing and subsequent molding of the polymer and articles produced therefrom. The reaction can be carried out in a batch or continuous process (reactive extrusion), and can be conducted without the addition or use of any solvent or catalyst.

In accordance with this discovery, it is an object of this invention to provide a method for producing a novel zein material that is resistant to solvents that normally dissolve unaltered zein and/or which exhibits increased tensile strength.

It is another object of this invention to provide a process for making solvent resistant zein materials in a single step using melt processing.

It is another object of this invention to provide a process for making solvent resistant zein materials using melt processing without the need for dissolving the zein in a solvent before processing.

Other objects and advantages of the invention will become readily apparent from the ensuing description.

DETAILED DESCRIPTION OF THE INVENTION

In accordance with applicant's process, zein can be rendered resistant to solvents that would normally dissolve unaltered zein and its tensile strength can be increased. Moreover, this process does not require a catalyst and can be conducted in a single step using melt processing, and thus can be conducted without the addition or use of any solvent. Without being limited thereto, the melt processed, PEMA cross-linked zein polymers of this invention exhibit limited solubility in known zein solvents, particularly acetic acid (AcOH), and/or increased tensile strength. As used herein, limited solubility is defined as less than or equal to approximately 75% by weight, of either the as-is extrudate (i.e., cross-linked zein polymer) or the polymer after further heating at elevated temperatures as described below, dissolving in the solvent when contacted therewith.

Figure 1:
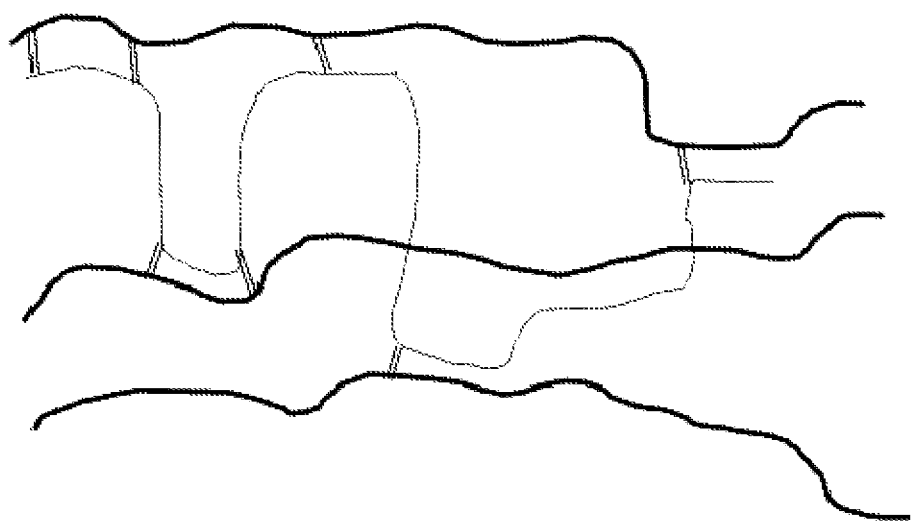
FIG. 1 shows an example of the structure of the zein cross-linked with PEMA with both intra- and inter-molecular cross-linking. The thick lines represents zein protein (three shown), while the thin lines represent PEMA and double-lines connecting the two represent bonds between the PEMA and zein (cross-links).
Figure 2:
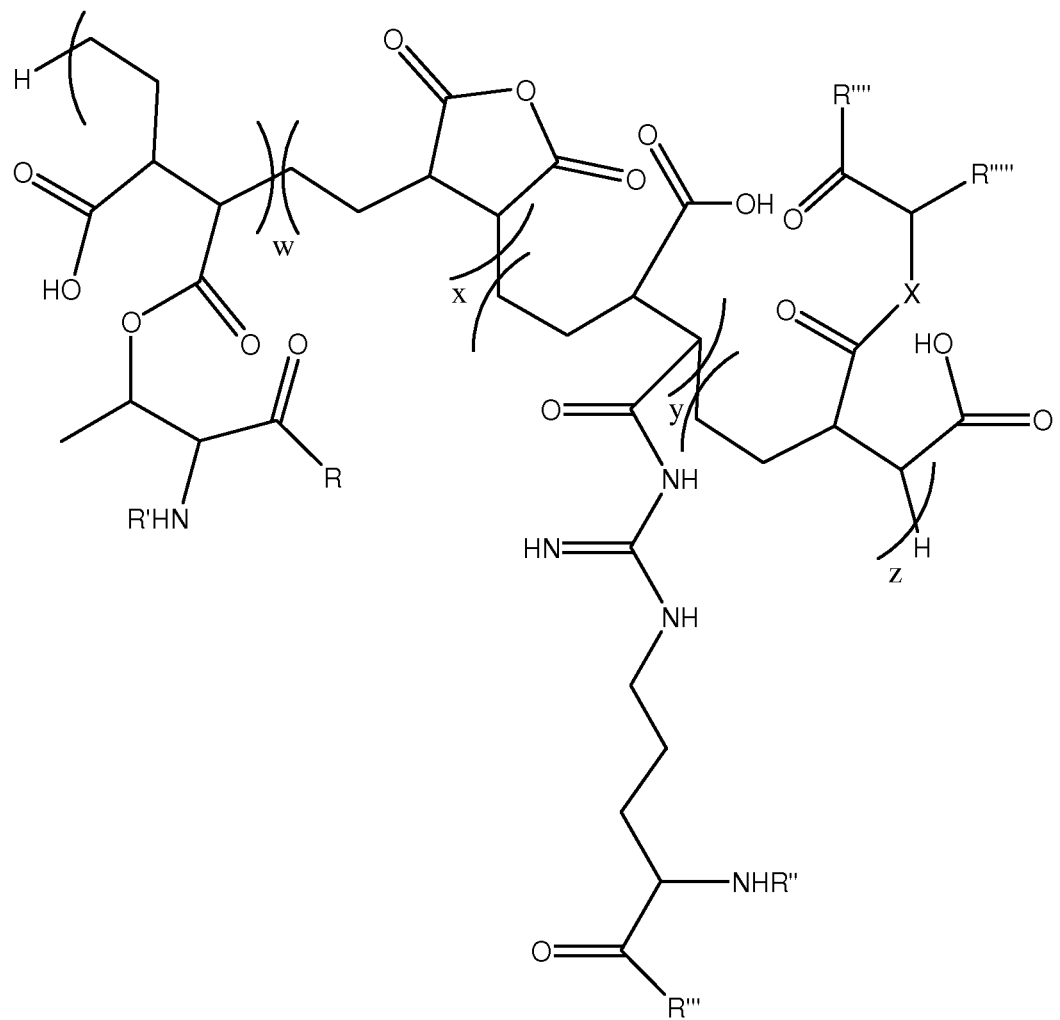
FIG. 2 shows another example of the structure of the zein cross-linked with PEMA, with the PEMA linked through different amino acids of the zein. The R and R' through R'''' represent the remaining portion of the zein protein molecules. Multiple anhydrides may be bound to the same or different zein proteins.
Figure 3A:
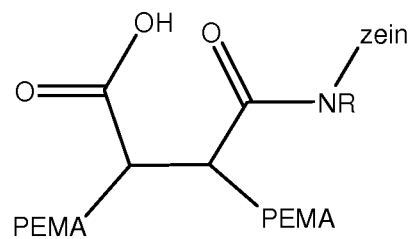
FIGS. 3A, B and C show different amino acids that may react with PEMA to form links. In (A), the amine on the protein chain end, tryptophan and arginine (R is either H or remainder of the tryptophan); in (B), the hydroxyls on serine, threonine and tyrosine; in (C), the thiol on cysteine.
Figure 3B:
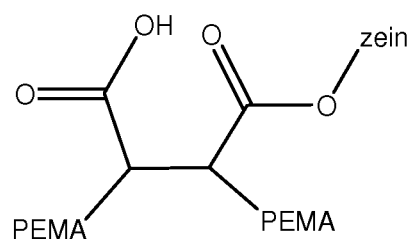
Figure 3C:
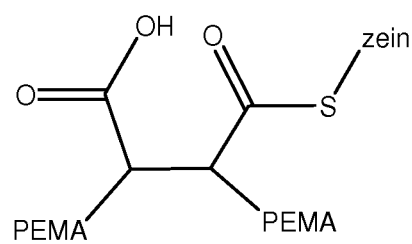

As noted above, the zein materials are produced by a melt process wherein the zein is mixed with PEMA, and preferably a plasticizer, under conditions of heat and shear effective to form a melt cross-linked zein. The term melt cross-linked as used herein, is consistent with its use in polymer chemistry, and broadly refers to the conversion of the solid phase zein to a flowable liquid phase. It is understood that a fully cross-linked material cannot be processed. However, as the term cross-linked is used herein, it describes the zein as branched (through the PEMA) to the extent that it has improved solvent resistance to known good solvents for zein (particularly AcOH) and/or improved tensile strength, yet it can still be processed using standard melt processing equipment and techniques that are used in the thermoplastic industry. As illustrated in FIGS. 1 and 2, the PEMA may form both inter- and intra-molecular cross-links with zein molecules. Moreover, the PEMA may react with different functional groups, including amine, hydroxyl or thiol, of various amino acids of the protein. Examples of such cross-links of PEMA with these amino acids are shown in FIGS. 2 and 3. As shown in FIG. 3 PEMA may react with the amine of tryptophan or arginine residues (FIG. 3A), the hydroxyls on serine, threonine and tyrosine (FIG. 3B), as well as the thiol of cysteine (FIG. 3C). It is understood that the structure shown in FIG. 2 is given merely by way of illustration and that the number, locations and types of cross-links of the PEMA with zein is highly variable.

The zein used in this process is preferably substantially pure, containing at least about 85% zein protein, most preferably above about 90% zein protein. In contrast to the above-mentioned, previously described processes for cross-linking zein, the zein is initially in a solid phase; it is not dissolved or suspended in a solvent such as ethanol or other alcohol prior to the reaction. The zein may be obtained from commercial sources or it may be extracted from maize, maize products, or maize by-products using techniques conventional in the art.

The PEMA is added to the zein in an amount effective to cross-link the zein and form the desired melt. The absolute amount of the PEMA used is somewhat variable depending upon the desired effect (i.e., increased solvent resistance or tensile strength), but should be at least 0.5% by weight of the zein. In a preferred embodiment, the PEMA is added in an amount between about 4% and about 15%, by weight of the zein (i.e., between about 40 mg up to about 150 mg PEMA per gram of zein). Further preferred amounts would be between 4% and about 8% by weight of the zein. In the most preferred formulation, the amount of PEMA would be between 6 and 8% by weight of the zein. PEMA amounts within the 4 to 15% range provide both increased solvent resistance and increased tensile strength. In contrast, PEMA amounts below 4% typically only provide increased tensile strength (i.e., at these lower amounts, the resultant zein articles have been found to have little improved solvent resistance against AcOH). Conversely, it is envisioned that higher amounts of PEMA may also be used, such as 20% by weight or higher, but are not preferred because higher amounts of PEMA may increase the cost of the article. Given that PEMA is a polymer, with essentially no vapor pressure, it is much safer than aldehydic reagents such as formaldehyde, glyoxal, glutaraldehyde and the like at improving the solvent resistance of zein.

In addition to the above-mentioned zein and PEMA, the addition of a plasticizer is particularly preferred. As used herein, plasticizer refers to a compound which lowers the glass transition temperature and the temperature needed to mechanically process the material (e.g., through an extruder). A variety of plasticizers are known in the polymer art and are suitable for use herein, including but not limited to triethylene glycol (TEG) and water, with TEG being preferred. The amount of plasticizer is not critical, but is typically added to the zein/PEMA reaction mixture in an amount effective to increase the flowability and thermoplasticity of the materials for ease of mixing and subsequent molding of the polymer and articles produced therefrom. The actual amount will vary with the particular plasticizer added and the temperature of the reaction, with higher temperatures requiring less plasticizer. By way of example and without being limited thereto, plasticizers such as TEG are added in an amount from 20% or less (by weight of the zein), with 1 to 20% being preferred, and 5 to 10% being particularly preferred. Using water as plasticizer, amounts are preferably between 3 to 15% by weight, of the zein.

The reaction should be conducted under conditions of temperature and shear (mixing) for a period of time effective to produce a melt of the cross-linked zein, preferably forming a sufficient number of branch points in the PEMA cross-linked polymer to impart improved solvent resistance and/or increased tensile strength relative to unaltered zein. The reaction temperature is variable with the reaction time and amount of plasticizer, and may be readily determined by routine experimentation. However, as a practical matter, low reaction temperatures require longer reaction times and consequently may not be economical. Reaction times are also practically limited by the short residence times for reactions conducted in continuous extruders, further limiting the minimum reaction temperature. For example, while it is envisioned that the reaction may be conducted at temperatures as low as 70° to 80° C., particularly in batch reactors where residence time is not limited, the required reaction time is nonetheless not economical. Thus, without being limited thereto, typical temperatures in the batch process, or in the final zone of the extruder, will preferably vary between about 140° and 240° C. Again, lower temperatures may be accessible if the reaction time is increased, although at lower temperatures, the PEMA may not be sufficiently melted. Higher temperatures may be used at shorter reaction times. However, if the temperature is too high for extended periods of time, the solvent durability is reduced as the protein degrades. In either case, a balance must be sought between completing the reaction and avoiding excessive protein degradation. The reaction time is also somewhat variable, and will vary with the temperature and reactor selected, and may be readily determined by the skilled practitioner. However, without being limited thereto, the reaction melt is preferably allowed to mix for between 0.5 and 20 minutes. Most preferably, the amount of time would be between 2 and 10 minutes.

The melt processing can take place in a batch mode or in a continuous mode. In a batch process, the zein, PEMA, and plasticizer are mixed while heating at a suitable temperature, preferably about 140° C. or higher, with shear (50 rpm, for example, using polymer appropriate rotors) and for a period of time effective (about 5-20 min) to form a cross-linked zein. In the batch process temperatures of 200° C. or higher may degrade the protein to the extent that solvent durability is reduced, and thus are not preferred. A variety of batch reactors are suitable for use herein, although a heated, mixing tank reactor such as a torque rheometer is preferred. For example, without being limited thereto, one particularly preferred rheometer is the Rheocord 90, produced by Haake Fisons, using the 600 mixing bowl and roller rotors (Thermo Electron Corporation, Madison, Wis.). When using this equipment, the desired amount of plasticizer (water, TEG or other) and then PEMA are both added to the zein. The mixture may be crudely mixed, such as with a spatula, and then added into the rheometer. Before addition, the rheometer should be preheated to the desired temperature and have the rotors turning at the desired rpm. After addition, the mixture is allowed to form a melt and processed for the desired period of time, typically between 5 and 20 minutes. After this period of time, the melt is removed from the device and cooled. After cooling the resin may be frozen with liquid nitrogen and ground into a fine powder. The powder may then be used to test for resistance to solvent, such as AcOH. Solvent resistance may be tested by placing approximately 1 grams of the powder in approximately 30 grams of AcOH and letting this stir for 20 hours at RT. If less than 75% dissolves, it is deemed as having improved resistance to solubilization relative to control (control is 98-100% soluble).

Although the reaction may be conducted in a batch mode, the melt processing is preferably conducted in a continuous mode. In this embodiment an extruder is preferred. When using reactive extrusion to modify zein, the zein feed will typically be added at the beginning of the screw. However, PEMA may be added with the zein at the beginning of the screw or at other locations down the screw. The plasticizer will be fed soon after zein addition. The zein melt may then be conveyed down the screw through mixing elements to where the PEMA is added (if it is not added with the zein). The screw rpm can be selected to obtain the desired degree of mixing and will vary with the particular extruder selected. By way of example and without being limited thereto, an rpm of approximately 150 rpm is typical. The screw design is generally such to provide a minimum of two zones of mixing, one after the addition of the plasticizer and one after the addition of the PEMA (if the PEMA is not added with the zein). The total time in the screw after addition of the PEMA is usually small, between about 2 and 5 minutes. The temperature along the screw can be varied, low to high, so that zein degradation is minimized, the cross-linking reaction is maximized and overall torque on the extruder is at such a level as to not power down the extruder. As the time exposed to elevated temperatures is reduced in reactive extrusion, the temperature in the final section of the screw can be higher than that which can be used in a batch process. Thus, the final zone of the extruder may be as high as 240° C. or more, but is preferably 230° C., more preferably no higher than 220° C.

A variety of extruders are suitable for use herein. However, in a preferred embodiment, a twin screw extruder having multiple injection ports is particularly convenient for conducting the reactive extrusion. Particularly preferred is the use of a twin screw extruder to which zein may be added, and then through one injection port there may be added plasticizer (such as 10% TEG by weight of zein), and through another port there may be added the PEMA (such as 6%, by weight of zein). This melt may then be processed through the extruder and exit the extruder with or without a die. The resulting pellets or rope may be ground or chopped to a suitable size for further testing. The ground extrudate can be tested for solvent durability in the same fashion as detailed in the testing of the ground material that was produced using the batch melt process.

By way of example and without being limited thereto, a Werner and Pfleiderer co-rotating ZSK30 twin screw extruder was used for initial compounding. Zein was added to this extruder at 60 gr/min. At the first injection port, TEG was added at approximately 7.14 gr/min (the exact amount of plasticizer will be dependent on the amount of PEMA that is being added; 6.67 gr/min for 0% PEMA [control] and 7.14 gr/min for 6% PEMA). At the second injection port, PEMA was added at 7.14 gr/min (if not added with the zein at the same time). The extruder can be run at 150 rpm. In this example, there are 8 independently controlled zones that were controlled to the following temperatures in degrees Celsius (the lowest temperature is nearest the zein feed and so on, this temperature pattern is for example only): 21, 85, 100, 135, 140, 210, 218, 218° C. respectively for zones 1-8. The extrudate was frozen and then ground using a Thomas Wiley mill to provide an appropriately sized mixture for solubility testing and compression molding.

The ground extrudate can then be tested for resistance to dissolution in AcOH by placing approximately 1 gram of the article in approximately 30 grams of AcOH and letting this stir for 20 hours at room temperature. As above, if less than 75% dissolves, it is deemed as being resistant to solubilization relative to control.

For compression molding of the extrudate from the extruder, the material may be ground using the technique as outlined earlier. The powder may then be used to make compression molded articles. In one trial, using extrudate from the twin-screw extruder, the mold produced four test samples, conforming to the ASTM D-638-V Standard, (Standard Test Method for Tensile Properties of Plastics, In 1999 Annual Book of ASTM Standards Plastics (I) section 8 D256-D2343; Vol. 8.01 ed.; Edited by Allen, Robert, Ed.; ASTM: West Conshohocken, Pa., 1999; pp 45-57.), at a time. Powder (1.5-1.8 g) was placed into each pocket of the mold. Molding conditions were selected to provide a tensile test sample that did not have visible remnants of the starting powder. The mold was heated at 116° C. for control and 138° C. for the item having 6% PEMA (intermediate temperatures are used for levels of PEMA between 0 and 6%) and 12,500 pounds force was applied in the Carver Model C press (Carver, Wabash, Ind.) for 20 min (after preheating the filled mold at temperature for 5 min prior to applying pressure). The mold was then removed from the Carver press. Samples were then tested on a standard physical property testing instrument (e.g. an Instron®) and it was found that with the incorporation of PEMA, the tensile strength increased.

In accordance with an optional yet preferred embodiment, the degree of solvent resistance of zein-PEMA articles produced by either a batch or continuous process can be improved by performing a heat treatment on the product of melt processing. This heat treatment should be above 100° C., preferably at about 135° C. for about one hour.

The following examples are intended only to further illustrate the invention and are not intended to limit the scope of the invention which is defined by the claims.

Examples 1-15

To 52.5 gr of zein (F4000 grade, Flo Chemical, Ashburnham, Mass.) is added the desired amount of PEMA and water. Formulation amounts and melt mixer conditions are detailed in Table 1. The mixture was crudely mixed with a spatula for approximately 1 minute. This mixture was then placed into a Haake Fission Torque Rheometer that had been pre-heated to the temperature indicated (between 160° and 200° C.). Roller rotors were used and were turning at 50 rpm. The resin was allowed to mix for 5 to 20 min. After the desired length of time, the resin was removed from the device, cooled, frozen in liquid nitrogen and ground on a Thomas Wiley mill (Thomas Scientific, Swedesboro, N.J.) to give a fine powder. One gram of this powder was then placed in 30 grams of AcOH and allowed to stir for 20 hours at RT. If less than 75% dissolves, then it is deemed as being resistant to solubilization. Detailed in Table 1 are the results of these solubilization tests.

was added between 0.3 and 4.3 gr/min of PEMA (see Table 2). The extruder can be run at 150 rpm using various temperature profiles (see Table 2 for samples profiles). The extrudate was collected as it exited the extruder—a 3 mm two hole die was used. The extrudate was ground using a Thomas Wiley mill to provide an appropriately sized mixture for compression molding or solvent resistance testing. Approximately 1 gram of the ground extrudate was then placed in 30 grams of AcOH and allowed to stir for 20 hours at RT. If more than 75% dissolves, it is not deemed resistant to solubilization. Detailed in Table 2 are the extrusion conditions, recipes and results of these solubilization tests.

For compression molding of the extrudate from the twin screw, 1.5 grams of the powder was added to each of the 4 positions of the mold, which would give samples having dimensions in accordance with the ASTM D-638-V Standard. The mold was then placed in a Carver Press where it was subjected to temperatures of between 115° and 138° C. after preheating the filled mold at temperature for 5 min and 12,500 pounds force was applied for 20 min. The samples were removed from the cooled mold. All samples having PEMA had improved tensile strength relative to control (Table 3).

TABLE 1

| Comparative Example Number | Reagent | Grams Zein | % Water Added | g Water Added | % PEMA | g PEMA | Time | Temp | RPM | % Solubility | Solvent Resistant |
|---|---|---|---|---|---|---|---|---|---|---|---|
| 1 | Control | 52.3 | 5 | 2.8 | 0 | 0 | 10 | 160 | 50 | 99 | No |
| 2 | Control | 52.3 | 5 | 2.8 | 0 | 0 | 5 | 180 | 50 | 99 | No |
| 3 | Control | 52.3 | 5 | 2.8 | 0 | 0 | 10 | 180 | 50 | 98 | No |
| 4 | Control | 52.3 | 5 | 2.8 | 0 | 0 | 20 | 180 | 50 | 100 | No |
| 5 | Control | 52.3 | 5 | 2.8 | 0 | 0 | 10 | 200 | 50 | 99 | No |
| 7 | PEM A | 52.3 | 5 | 2.8 | 2% | 1.05 | 10 | 180 | 50 | 96 | No |
| 8 | PEM A | 52.3 | 5 | 2.8 | 4% | 2.09 | 10 | 180 | 50 | 92 | No |
| 9 | PEM A | 52.3 | 5 | 2.8 | 4% | 2.09 | 20 | 180 | 50 | 93 | No |
| 10 | PEM A | 52.3 | 5 | 2.8 | 6% | 3.14 | 10 | 160 | 50 | 38 | Yes |
| 11 | PEM A | 52.3 | 5 | 2.8 | 6% | 3.14 | 5 | 180 | 50 | 37 | Yes |
| 12 | PEM A | 52.3 | 5 | 2.8 | 6% | 3.14 | 10 | 180 | 50 | 64 | Yes |
| 13 | PEM A | 52.3 | 5 | 2.8 | 6% | 3.14 | 20 | 180 | 50 | 90 | No |
| 14 | PEM A | 52.3 | 5 | 2.8 | 6% | 3.14 | 10 | 200 | 50 | 84 | No |
| 15 | PEM A | 52.3 | 5 | 2.8 | 8% | 4.18 | 10 | 180 | 50 | 55 | Yes |

Examples 16-25

Shown in Table 2 are the extrusion conditions and composition information for examples 16-25. To the feed throat of a Werner and Pfleiderer co rotating ZSK30 twin screw extruder was added 60 gr/min of zein. To this material through the first injection port was added between 6.70 and 7.14 gr/min of TEG (see Table 2). To this material through the second port

TABLE 2

| Item | Grams/Min Zeing | % Zein | grams/min TEG | % TEG | grams/min PEMA | % PEMA | rpm | Temps | % Soluble | Solvent Resistant |
|---|---|---|---|---|---|---|---|---|---|---|
| 16 | 60.0 | 90% | 6.7 | 10% | 0.0 | 0.0% | 150 | Profile A | 100 | No |
| 17 | 60.0 | 89% | 6.7 | 10% | 0.3 | 0.5% | 150 | Profile A | 98 | No |
| 18 | 60.0 | 89% | 6.7 | 10% | 0.7 | 1.0% | 150 | Profile A | 96 | No |
| 19 | 60.0 | 88% | 6.8 | 10% | 1.4 | 2.0% | 150 | Profile A | 94 | No |
| 20 | 60.0 | 86% | 7.0 | 10% | 2.8 | 4.0% | 150 | Profile A | 75 | Yes |
| 21 | 60.0 | 84% | 7.1 | 10% | 4.3 | 6.0% | 150 | Profile A | 46 | Yes |
| 22 | 60.0 | 90% | 6.7 | 10% | 0.0 | 0.0% | 150 | Profile B | 99 | No |
| 23 | 60.0 | 84% | 7.1 | 10% | 4.3 | 6.0% | 150 | Profile B | 73 | Yes |
| 24 | 61.0 | 89% | 6.7 | 10% | 0.0 | 0.0% | 150 | Profile C | 99 | No |
| 25 | 60.0 | 84% | 7.1 | 10% | 4.3 | 6.0% | 150 | Profile C | 73 | Yes |

Profile A = 21, 85, 100, 135, 140, 210, 218, 218° C.
Profile B = 21, 85, 110, 155, 160, 245, 260, 260° C.
Profile C = 21, 85, 100, 116, 138, 160, 180, 180° C.

TABLE 3

| Item | % Zein | % TEG | % PEMA | Temps | Tensile Str. (MPa) | S.D. Tensile Str. |
|---|---|---|---|---|---|---|
| 16 | 90% | 10% | 0.0% | Profile A | 12.5 | 2.2 |
| 17 | 89% | 10% | 0.5% | Profile A | 19.3 | 2.6 |
| 18 | 89% | 10% | 1.0% | Profile A | 23.2 | 1.9 |
| 19 | 88% | 10% | 2.0% | Profile A | 19.5 | 1.8 |
| 20 | 86% | 10% | 4.0% | Profile A | 20.5 | 1.3 |
| 21 | 84% | 10% | 6.0% | Profile A | 26.4 | 4.1 |

It is understood that the foregoing detailed description is given merely by way of illustration and that modifications and variations may be made therein without departing from the spirit and scope of the invention.

I claim:

1. A polymer comprising zein cross-linked with polyethylene maleic anhydride, wherein said polymer is produced by a process comprising mixing zein with polyethylene maleic anhydride in an amount effective to cross-link said zein and heating at a temperature with shear and for a period of time effective to form a melt comprising said zein and polyethylene maleic anhydride and cross-link said zein and polyethylene maleic anhydride; wherein said process does not utilize aldehydic reagents.

2. An article of manufacture comprising a polymer, wherein said polymer comprises zein cross-linked with polyethylene maleic anhydride, wherein said polymer is produced by a process comprising mixing zein with polyethylene maleic anhydride in an amount effective to cross-link said zein and heating at a temperature with shear and for a period of time effective to form a melt comprising said zein and polyethylene maleic anhydride and cross-link said zein and polyethylene maleic anhydride; wherein said process does not utilize aldehydic reagents.

3. A process for producing a polymer according to claim 1, comprising mixing zein with polyethylene maleic anhydride in an amount effective to cross-link said zein and heating at a temperature with shear and for a period of time effective to form a melt comprising said zein and polyethylene maleic anhydride and cross-link said zein and polyethylene maleic anhydride.

4. The process of claim 3, wherein said zein comprises a solid phase.

5. The process of claim 4, wherein said zein is substantially pure.

6. The process of claim 3, wherein said amount of said polyethylene maleic anhydride comprises at least 0.5% by weight of said zein.

7. The process of claim 6, wherein said amount of said polyethylene maleic anhydride comprises between 4% and 8%, by weight of said zein.

8. The process of claim 3, wherein said temperature is between 140° C. and 240° C.

9. The process of claim 3, wherein said temperature is between 160° C. and 220° C.

10. The process of claim 3, wherein said mixing and heating are conducted in an extruder.

11. The process of claim 10, wherein said mixing and heating in said extruder are conducted in a continuous mode.

12. The process of claim 3, wherein said mixing and heating is conducted in a batch reactor.

13. The process of claim 3, wherein said mixing further includes a plasticizer.

14. The process of claim 13, wherein said plasticizer is provided in an amount up to about 20%, by weight, of said zein.

15. The process of claim 3, wherein said period of time is between 0.5 and 20 minutes.

16. A melt processed cross-linked zein polymer produced by the process of claim 3.

17. A melt processed cross-linked zein polymer produced by the process of claim 6.

18. A melt processed cross-linked zein polymer produced by the process of claim 7.

19. A melt processed cross-linked zein polymer produced by the process of claim 8.

20. A melt processed cross-linked zein polymer produced by the process of claim 11.

21. A melt processed cross-linked zein polymer produced by the process of claim 13.

22. A melt processed cross-linked zein polymer produced by the process of claim 14.

23. A polymer comprising zein cross-linked with polyethylene maleic anhydride, wherein said polymer is produced by a process consisting of mixing zein with polyethylene maleic anhydride in an amount effective to cross-link said zein and heating at a temperature with shear and for a period of time effective to form a melt comprising said zein and polyethylene maleic anhydride and cross-link said zein and polyethylene maleic anhydride.

24. An article of manufacture comprising a polymer, wherein said polymer comprises zein cross-linked with polyethylene maleic anhydride, wherein said polymer is produced by a process consisting of mixing zein with polyethylene maleic anhydride in an amount effective to cross-link said zein and heating at a temperature with shear and for a period of time effective to form a melt comprising said zein and polyethylene maleic anhydride and cross-link said zein and polyethylene maleic anhydride.

* * * * *